United States Patent [19]

Olah

[11] Patent Number: 4,523,040

[45] Date of Patent: Jun. 11, 1985

[54] METHYL HALIDES AND METHYL ALCOHOL FROM METHANE

[76] Inventor: George A. Olah, 2252 Gloaming Way, Beverly Hills, Calif. 90210

[21] Appl. No.: 494,915

[22] Filed: May 16, 1983

Related U.S. Application Data

[63] Continuation of Ser. No. 298,390, Sep. 1, 1981, abandoned.

[51] Int. Cl.$^3$ .................... C07C 41/01; C07C 27/00; C07C 29/00
[52] U.S. Cl. .................................. 568/671; 568/891; 568/893; 568/840; 570/253; 570/254; 570/255
[58] Field of Search .............. 568/891, 840, 893, 671; 570/123, 161, 168, 253, 254, 255

[56] References Cited

U.S. PATENT DOCUMENTS

| | | |
|---|---|---|
| 1,086,381 | 2/1914 | Masland . |
| 1,591,984 | 7/1926 | Krause et al. . |
| 1,688,726 | 10/1928 | McKee . |
| 1,723,442 | 8/1929 | Roka . |
| 2,156,039 | 4/1939 | Dachlauer et al. . |
| 3,172,915 | 3/1965 | Borkowski et al. . |
| 3,562,321 | 2/1971 | Borkowski et al. . |

FOREIGN PATENT DOCUMENTS

| | | |
|---|---|---|
| 1017152 | 1/1966 | United Kingdom . |
| 1104294 | 2/1968 | United Kingdom . |
| 388529 | 4/1976 | U.S.S.R. . |

OTHER PUBLICATIONS

Olah, J. Am. Chem. Soc., 95, (1973), pp. 7686-7692.
Olah, Friedel-Crafts and Related Reactions, Interscience Publishers, New York, 1963, p. 26.
Nafion pamphlet, Du Pont, Apr. 1928, Perfluorosulfonic Acid Products.

Primary Examiner—Howard T. Mars
Attorney, Agent, or Firm—Pennie & Edmonds

[57] ABSTRACT

This invention relates to solid acidic or metal catalyst-promoted halogenation of methane to produce methyl monohalides in high selectivity. Concurrent or simultaneous hydrolysis provides methyl alcohol and/or dimethyl ether in good yields.

11 Claims, No Drawings

METHYL HALIDES AND METHYL ALCOHOL FROM METHANE

This is a continuation of application Ser. No. 298,390 filed Sept. 1, 1981, now abandoned.

TECHNICAL FIELD

This invention relates to solid acidic or metal catalyst-promoted halogenation of methane to produce methyl monohalides in high selectivity. Concurrent or simultaneous hydrolysis provides methyl alcohol and/or dimethyl ether in good yields.

BACKGROUND ART

The selective conversion of methane into its monofunctional derivatives, such as methyl halides or methyl alcohol, is highly desirable, but in practice has not been achieved on any practical basis.

The chlorination of methane is an industrial process practiced on a large scale. The reaction is a strongly exothermic one which takes place via free radicals and is generally conducted without supplying heat and usually in the absence of a catalyst at 400°–450° C. under slightly elevated pressures. The chlorination is normally thermally initiated via homolysis of chlorine molecules to chlorine atoms; the process can also be operated photochemically. For surveys of these processes, it is appropriate to refer to F. Asinger "Paraffins. Chemistry and Technology", Pergamon Press, New York, 1968; M. L. Poutsma "Methods in Free Radical Chemistry", Vol. II, E. S. Huyser, Ed., M. Dekker, New York, 1969; and R. Weissermel and H. J. Arpe "Industrial Organic Chemistry", Verlag Chemie, 1978, pp. 46–47. By these reactions, all of the possible chlorinated methanes are usually formed together when an equimolar $Cl_2/CH_4$ ratio is employed:

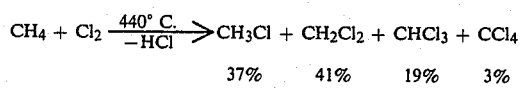

$$CH_4 + Cl_2 \xrightarrow[-HCl]{440° C.} CH_3Cl + CH_2Cl_2 + CHCl_3 + CCl_4$$
$$\phantom{CH_4 + Cl_2 \xrightarrow[-HCl]{440° C.}} 37\% \quad 41\% \quad 19\% \quad 3\%$$

If methyl chloride is the preferred product, a large excess of methane (approx. tenfold) must be used, as methyl chloride is more rapidly chlorinated than methane under free radical conditions. There are normally many by-products of the chlorination of methane, such as hexachloroethane and small amounts of trichloroethylene.

Methyl alcohol is increasingly important not only as a chemical raw material and building block for such products as formaldehyde, acetic acid, vinyl acetate, ethylene glycol and others, but also via its condensation reactions to give gasoline or hydrocarbons, such as olefins, aromatics and the like. Its direct use as a transportation fuel is also gaining importance. A whole scope of so-called $C_1$ chemistry is based primarily on methyl alcohol.

Methyl alcohol, once produced from wood fermentation (i.e., wood alcohol), is, at the present time, nearly exclusively produced from CO and $H_2$ (synthesis gas) derived from coal or natural gas. Coal or methane first must be converted in an energy consuming step into syn-gas, which is then, in a second energy consuming step under pressure and generally forcing conditions, converted into methyl alcohol. Clearly, direct oxidative conversion of methane into methyl alcohol would be highly desirable. Despite continued efforts no such process was, however, previously achieved on a practical scale.

The oxidation of methane generally is not selective. In the past, many attempted oxidations concentrated on manufacturing formaldehyde from methane. The low rate of reaction of $CH_4$ at temperatures below 600° C. coupled with the high rate of decomposition of formaldehyde above 600° C. is probably the reason that no industrial process has been developed to date. Decomposition of formaldehyde could only be avoided be extremely short residence times. Such a process has been recently described involving partial oxidation of methane to methyl alcohol and formaldehyde. The residence time is $1.55 \times 10^{-3}$ sec. and the pressure 60 atm., respectively (Huels). However, oxidation of methane, similarly to chlorination, is free radical chain reaction, which explains the observed lack of selectivity.

I have previously described in the *Journal of the American Chemical Society*, Vol. 95, 7686 (1973) that, under specific conditions, alkanes can undergo electrophilic chlorination and chlorinolysis. With a $SbF_5$ catalyst in $SO_2ClF$ solution at $-78°$ or at room temperature with a reaction time of 24 hours, methane was transformed qualitatively to methyl chloride. No practical yields were obtained. $AlCl_3$ catalyst gave under similar conditions 1% methyl chloride. These reactions clearly did not represent a practical method for the chlorination of methane.

SUMMARY AND DESCRIPTION OF THE INVENTION

The present invention relates to a process for the selective halogenation of methane to produce methyl halides and through their hydrolysis methyl alcohol and/or dimethyl ether.

THE CATALYSTS

Either (i) solid strongly acidic catalysts or, (ii) supported Group VIII metal (particularly platinum and palladium) catalysts are capable of catalyzing the gas-phase halogenation of methane predominantly to methyl monohalides in 85 to 99% selectivity. Subsequent or concurrent catalytic hydrolysis gives methyl alcohol and/or dimethyl ether.

A particularly useful class of solid, strongly acidic catalysts are those derived from halides, oxyhalides, oxides, sulfides and oxysulfides of metals, particularly transition metals of Groups, IV, V, VI, VIII of the Periodic Table, such as of tantalum, niobium, zirconium, tungsten, titanium, chromium and the like, or mixtures thereof, deposited on suitable chalconite carriers, such as alumina, zirconia or silica-alumina. These catalysts are capable of effecting the ready conversion of methane to methyl halides.

As noted in Olah, G. A. "Friedel-Crafts Chemistry," N.Y., Wiley-Interscience, 1973. p. 343-344, the elements of Group VIA such as oxygen, sulfur, selenium or tellurium, have been called "chalcogens", and compounds containing these elements are called "chalconites", "chalcogenides" or "chalcides." A variety of solid oxides and sulfides, especially those comprising alumina, silica and mixtures of alumina and silica, either natural or synthetic, in which other oxides such as chromia, magnesia, molybdena, thoria, tungstic oxide, zirconia, etc., may also be present, as well as sulfides of molybdenum are useful chalconite carriers. Many naturally occurring compositions exist for use as the carriers including: bauxite, floridin, Georgia clay, and other natural aluminosilicates.

Synthetic chalconites, other than those of the silica-alumina type, representative of the chalconite carriers are: BeO, $Cr_2O_3$, $P_2O_5$, $ThO_2$, $TiO_2$, $Al_2(SO_4)_3$ (which may be regarded as $Al_2O_3.3SO_3$), $Al_2O_3.Cr_2O_3$, $Al_2O_3.Fe_2O_3$, $Al_2O_3.CoO$, $Al_2O_3.MnO$, $Al_2O_3.V_2O_3$, $Al_2O_3.Mo_2O_3$, $Cr_2O_3.Fe_2O_3$, $MoS_2$, and $MoS_3$.

The acidic chalconite supports are physically and chemically stable. They are generally catalytically active at only higher temperatures, as their acidity is not great enough to lead them to form stable complexes with unsaturated compounds, as do the aluminum halides, for example.

The supported Group VIII metal catalysts include the various Group VIII metals supported on suitable chalconite carriers. Particularly useful are platinum and palladium supported on alumina, silica, barium sulfate or related carriers.

THE PROCESS CONDITIONS

It is my invention that a practical process has been found for the selective acidic or metal catalyzed halogenation of methane to methyl monohalides (chloride, bromide, iodide or fluoride).

The acid halogenations are carried out over solid acidic catalysts, particularly supported metal-based catalysts, preferably selected from transition metal halides, oxides or oxyhalides, such as those of iron, tantalum, niobium or zirconium, on alumina, baria, or other neutral oxides, barium sulfate or related carriers, at temperatures between about 100° to 500° C., preferably between 200° and 325° C.

Metal catalyzed reactions are carried out over supported metal catalysts, preferably of the Group VIII metals, on alumina, baria, or other neutral oxides, barium sulfate or related carriers, at temperatures between 100° and 350° C., preferably between 200°–300° C.

The solid acidic reactions are considered to take place via surface catalytic activation of chlorine, bromine, or iodine to an electrophilic halogen species. The selective nature of the reactions is reflected by the fact that even when using an excess of halogen (methane to chlorine ratio of 1:2 to as high as 1:8), methyl halides are formed in 85 to >99% selectivity over methylene halides.

At the same time, highly selective (99%) monochlorination is readily achieved when reacting excess methane (methane to chlorine ratio from 1:1 to 8:1) over the same catalysts. Excess methane under these conditions is also a diluent for the system and eliminates any potentially explosive mixtures.

It is a further part of my invention that similar selective monohalogenation of methane was also discovered to be possible using supported metal catalysts on alumina, baria, or other neutral oxides, barium sulfate or related carriers. In these reactions, an intermediate insertion of the metal in a C-H bond is premised with subsequent chlorinolysis.

In a similar fashion bromination and iodination of methane can also be achieved both in acid catalyzed electrophilic and metal promoted halogenations.

Fluorination of methane is also possible, but necessitates high dilution, preferably with an inert gas, and handling difficulties associated with the use of elemental fluorine.

Hydrogen chloride, bromide and iodide by-products of the reactions can be readily recycled via oxyhalogenation and thus reused.

Methyl halides formed in the selective halogenations disclosed in my invention can be used, according to my co-pending application Ser. No. 290,292, now U.S. Pat. No. 4,373,109 in the production of lower olefins and hydrocarbons of the gasoline range, when treated over bifunctional acidic-basic catalysts.

The methyl halides readily obtainable in high yield and selectivity according to my invention are also conveniently used via their hydrolysis either under thermal or catalytic conditions, to produce methyl alcohol and/or dimethyl ether. The conversion of methane to methyl alcohol can be accordingly carried out as a two-step process, but also can be practiced as a single-step process converting methane directly to methyl alcohol (and/or dimethyl ether) when reacting methane in the presence of water (steam) with halogens. In this application, acidic oxides or oxyhalides, compatible with water, are preferred.

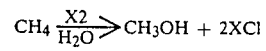

$$CH_4 \xrightarrow[H_2O]{X_2} CH_3OH + 2XCl$$

As hydrogen halides (X=Cl, Br, I) can be readily recycled via oxyhalogenation, the disclosed process represents a viable and energy saving alternative to the production of methyl alcohol from CO and $H_2$, i.e., syngas.

In all of the reactions discussed, the catalyst is preferably present in an amount of 0.1 to 25% based on the amount of methane.

The following examples are illustrative and are set forth for the purpose of illustration only and are not to be construed as limiting the scope of the invention in any manner. In the related Tables, the product compositions have been normalized, even if not stated, to provide 100 percent conversion, excluding unreacted methane which can be recycled.

EXAMPLE 1

A mixture of methane and chlorine in the molar ratios indicated, was reacted over a 20% tantalum oxyfluoride catalyst deposited on alumina in a continuous flow reactor at 235° C. to 300° C., respectively. The conversions per pass and product compositions were as follows:

| Reaction Temp. °C. | 235 | 235 | 300 | 240 | 240 | 240 |
|---|---|---|---|---|---|---|
| $CH_4:Cl_2$ ratio | 1:2 | 1:4 | 1:2 | 2:1 | 4:1 | 8:1 |
| % Conversion | 13* | 88* | 40* | 91** | 95** | 99** |

*based on methane
**based on chlorine

| | % Product composition | | | | | |
|---|---|---|---|---|---|---|
| methyl chloride | 75 | 96.5 | 90 | 99 | 99 | 99 |
| methylene chloride | — | trace | 10 | trace | trace | trace |
| ethane | 25 | — | trace | — | — | — |
| ethyl chloride | — | 3.5 | — | — | — | — |

EXAMPLE 2

Methane and chlorine in a molar ratio of 1:2 were passed at 250° C. over a 20% niobium oxyfluoride catalyst supported on alumina. The product composition obtained with 39% conversion was the following:

| % Product composition | |
|---|---|
| methyl chloride | 98 |
| methylene chloride | 2 |

EXAMPLE 3

Methane and chlorine in a molar ratio of 1:4 were passed over a 20% zirconium oxyfluoride catalyst on alumina in a continuous flow reactor at 270° C. With 30% conversion per pass the following product composition was obtained:

| % Product composition | |
|---|---|
| methyl chloride | 96.5 |
| methylene chloride | 3.5 |

EXAMPLE 4

A mixture of methane and chlorine in a molar ratio of 1:4 was reacted over a 20% antimony oxyfluoride catalyst deposited on alumina at 250° C. A 19% conversion per pass gave the following product composition:

| % Product composition | |
|---|---|
| methyl chloride | 86 |
| methylene chloride | 5 |
| ethyl chloride | 9 |

EXAMPLE 5

A 1:2 molar mixture of methane and bromine was reacted in the presence of a 20% antimony oxyfluoride catalyst supported on alumina at 200° C. With a 36% conversion per pass, the following product composition was obtained:

| % Product composition | |
|---|---|
| methyl bromide | 87 |
| ethylene bromide | 3 |
| ethyl bromide | 0.5 |
| butanes | 9.5 |

EXAMPLE 6

A 1:3 molar mixture of methane and chlorine was passed at 250° C. over a 1% iron catalyst supported on alumina with a 59% conversion per pass. The following product composition was obtained:

| % Product composition | |
|---|---|
| methyl chloride | 97 |
| ethyl chloride | 3 |

EXAMPLE 7

Methane and chlorine were passed over a 0.5% platinum catalyst deposited on alumina. The conversions and product composition obtained were the following:

| Reaction Temp. °C. | 200 | 200 | 250 | 250 |
|---|---|---|---|---|
| CH$_4$:Cl$_2$ ratio | 1:2 | 1:1 | 2:1 | 4:1 |
| % Conversion | 50* | 44* | 74** | 82** |

*based on methane
**based on chlorine

| % Product composition | | | | |
|---|---|---|---|---|
| methyl chloride | 92 | 99 | 99 | 99 |
| methylene chloride | 8 | trace | trace | trace |

EXAMPLE 8

Methane and chlorine were passed at 200° C. over a 0.5 palladium catalyst deposited on barium sulfate. The conversions and product composition obtained were the following:

| Reaction Temp. °C. | 200 | 200 |
|---|---|---|
| CH$_4$:Cl$_2$ ratio | 1:2* | 2:1** |
| % Conversion | 29 | 69 |

*based on methane
**based on chlorine

| % Product composition | | |
|---|---|---|
| methyl chloride | 99 | 99 |
| ethylene chloride | trace | trace |

EXAMPLE 9

A 1:1:1 molar mixture of methane, bromine and water was reacted over a 20% tantalum oxyfluoride catalyst supported on alumina at 260° C. With a 77% conversion, the following product composition was obtained:

| methyl bromide | 64% |
|---|---|
| methyl alcohol + dimethyl ether | 31% |
| ethyl bromide | 3% |
| C$_3$ + C$_4$ | 2% |

EXAMPLE 10

A 1:1:1 molar mixture of methane, chlorine and water was reacted over a 20% tungsten oxide on alumina catalyst at 250° C. With a 49% conversion, the following product distribution was obtained.

| methyl chloride | 68% |
|---|---|
| methyl alcohol + dimethyl ether | 24% |
| ethyl chloride | 6% |
| methylene chloride | trace |
| C$_3$ + C$_4$ | 2% |

EXAMPLE 11

A 1:5 molar mixture of methyl chloride and steam was passed, in a continuous flow reactor, over a catalyst composed of 10% zinc oxide on alumina containing 10% aluminum hydroxide at 385° C. A 29% conversion per pass of methyl alcohol was obtained with 98% selectivity.

EXAMPLE 12

Under conditions of Example 11, when carrying out the reaction with a catalyst composed of 10% magnesium oxide on alumina containing 10% aluminum hydroxide at 420° C., a 21% conversion of methyl alcohol was obtained with 98% selectivity.

EXAMPLE 13

Under conditions of Example 11, when carrying out the reaction with a catalyst composed of 10% titanium oxide on alumina containing 10% aluminum hydroxide, a 18% conversion to methyl alcohol was obtained with 98% selectivity.

I claim:

1. A process for the catalytic production of methyl monohalides from methane, such process exhibiting 85 to 99% selectivity, consisting essentially of reacting methane with a halogen selected from chlorine, bromine or iodine at a temperature between about 100° and 325° C. in the presence of a solid acid catalyst from the Group IVB, VB or VIB transition metal oxides or oxyhalides supported on a chalconite carrier.

2. The process of claim 1 wherein the transition metal is tantalum, niobium, zirconium or titanium and the chalconite carrier is alumina.

3. A process for the catalytic production of methyl monohalides from methane, such process exhibiting 85 to 99% selectivity, consisting essentially of reacting methane with a halogen selected from chlorine, bromine or iodine at a temperature between about 100° and 350° C. in the presence of a solid catalyst from a Group VIII metal supported on a chalconite carrier.

4. The process of claim 3 wherein the Group VIII metal is platinum or palladium.

5. The process of claim 3 wherein the chalconite carrier is alumina, silica or barium sulfate.

6. A process for producing methyl alcohol and by the reaction of methane, halogen selected from chlorine, bromine or iodine, and water at a temperature between about 100° and 325° C. in the presence of a catalyst from the group IVB, VB or VIB transition metal oxides or oxyhalides supported on a chalconite carrier.

7. The process of one of claims 1 or 3 wherein the catalyst is present in amount of between 0.1 and 25% by weight based on the amount of methane.

8. A process of claim 1 including the further step of hydrolyzing the methyl monohalide obtained to methyl alcohol and/or dimethyl ether.

9. A process of claim 3 including the further step of hydrolyzing the methyl monohalide obtained to methyl alcohol and/or dimethyl ether.

10. A process of claim 1 in which the halogen is chlorine or bromine.

11. A process of claim 3 in which the halogen is chlorine or bromine.

* * * * *